United States Patent
Chmeissani Raad (10) Patent No.: US 11,766,228 B2
(45) Date of Patent: Sep. 26, 2023

(54) DEVICES, SYSTEMS, AND METHODS FOR MAMMOGRAPHY WITH A DETECTOR HAVING REDUCED DIMENSIONS

(71) Applicant: INSTITUT DE FÍSICA D'ALTES ENERGIES (IFAE), Barcelona (ES)

(72) Inventor: Mokhtar Chmeissani Raad, Barcelona (ES)

(73) Assignee: INSTITUT DE FÍSICA D'ALTES ENERGIES (IFAE), Barcelona (ES)

( * ) Notice: Subject to any disclaimer, the term of this patent is extended or adjusted under 35 U.S.C. 154(b) by 142 days.

(21) Appl. No.: 17/467,621

(22) Filed: Sep. 7, 2021

(65) Prior Publication Data
US 2022/0071583 A1   Mar. 10, 2022

(30) Foreign Application Priority Data

Sep. 7, 2020   (EP) .................................... 20382794

(51) Int. Cl.
*A61B 6/00* (2006.01)
*A61B 6/04* (2006.01)
*G01T 1/24* (2006.01)

(52) U.S. Cl.
CPC ............ *A61B 6/502* (2013.01); *A61B 6/0435* (2013.01); *A61B 6/4241* (2013.01); *A61B 6/481* (2013.01);
(Continued)

(58) Field of Classification Search
CPC ..... A61B 6/0435; A61B 6/4241; A61B 6/481; A61B 6/483; A61B 6/502; A61B 6/5282; G01T 1/241; G01T 1/244; G01T 1/247
See application file for complete search history.

(56) References Cited

U.S. PATENT DOCUMENTS

| | | | | |
|---|---|---|---|---|
| 5,418,833 A | * | 5/1995 | Logan | G21K 1/10 |
| | | | | 378/154 |
| 5,539,797 A | * | 7/1996 | Heidsieck | A61B 6/02 |
| | | | | 378/37 |

(Continued)

FOREIGN PATENT DOCUMENTS

| EP | 3690490 A1 | | 8/2020 |
|---|---|---|---|
| JP | 2014113226 A | | 6/2014 |
| JP | 2014113226 A | * | 6/2014 |

OTHER PUBLICATIONS

Extended European Search Report for European Application No. 20382794.4, dated Feb. 5, 2021, 6 pages.

*Primary Examiner* — Blake C Riddick
(74) *Attorney, Agent, or Firm* — Edell, Shapiro & Finnan, LLC (57) ABSTRACT

An auxiliary device attachable to a mammography machine having an X-ray source and an X-ray receptor having a receptor area. The auxiliary device includes a housing having a length, width, and thickness, wherein the length and width of the housing are adapted to a length and width of the receptor area. The auxiliary device further includes one or more attachments for attaching the auxiliary device to the mammography machine, and a detector inside the housing. The detector includes a slab of semiconductor material, an electrode on a first side of the slab, and a pixelated electrode detector on the second side of the slab, and a read-out circuit bonded to the pixelated electrode detector, and the read-out circuit being configured for spectral photon counting with two or more energy bins. Methods for medical imaging are also provided.

19 Claims, 5 Drawing Sheets

(52) U.S. Cl.
CPC ............ *A61B 6/483* (2013.01); *A61B 6/5282* (2013.01); *G01T 1/241* (2013.01); *G01T 1/244* (2013.01); *G01T 1/247* (2013.01)

(56) References Cited

U.S. PATENT DOCUMENTS

| | | | | |
|---|---|---|---|---|
| 6,292,531 | B1* | 9/2001 | Hsieh | A61B 6/4028 378/22 |
| 6,592,257 | B1* | 7/2003 | Heidsieck | G03B 42/025 378/189 |
| 7,386,091 | B2* | 6/2008 | Hoheisel | A61B 6/4233 378/189 |
| 2003/0194050 | A1* | 10/2003 | Eberhard | A61B 6/502 378/37 |
| 2004/0234026 | A1* | 11/2004 | Shoji | A61B 6/502 378/37 |
| 2005/0063509 | A1* | 3/2005 | Defreitas | A61B 6/585 378/37 |
| 2005/0111617 | A1* | 5/2005 | Shoji | A61B 6/4411 378/37 |
| 2006/0098777 | A1* | 5/2006 | Hoheisel | A61B 6/4233 378/98.8 |
| 2006/0126794 | A1* | 6/2006 | Hermann | A61B 6/0414 378/180 |
| 2011/0021947 | A1* | 1/2011 | Nakayama | A61B 6/469 378/37 |
| 2011/0253901 | A1* | 10/2011 | Chmeissani Raad | G01T 1/249 250/370.09 |
| 2013/0182823 | A1* | 7/2013 | Kuwabara | A61B 6/542 378/91 |
| 2014/0119495 | A1* | 5/2014 | Jang | A61B 6/4007 378/4 |
| 2014/0364743 | A1* | 12/2014 | Godavarty | G01N 21/359 600/473 |
| 2015/0139526 | A1* | 5/2015 | Jeong | A61B 6/5217 382/132 |
| 2016/0310087 | A1* | 10/2016 | Myrman | A61B 6/06 |
| 2017/0347972 | A1* | 12/2017 | Hjarn | A61B 6/027 |
| 2017/0350990 | A1* | 12/2017 | Chmeissani Raad | G01T 1/366 |
| 2018/0240842 | A1 | 8/2018 | Meylan et al. | |

* cited by examiner

DEVICES, SYSTEMS, AND METHODS FOR MAMMOGRAPHY WITH A DETECTOR HAVING REDUCED DIMENSIONS

CROSS-REFERENCE TO RELATED APPLICATIONS

The present application relates to and claims the benefit and priority to European Application No. 20382794.4, filed Sep. 7, 2020, which is herein incorporated by reference in its entirety.

FIELD

The present disclosure relates to medical imaging, and more particularly the present disclosure relates to imaging techniques useful for mammography. The present disclosure relates to auxiliary imaging devices for mammography machines and to methods relying on photon counting of a region of interest.

BACKGROUND

Breast Cancer is the leading cause of death for women and is the second most common cause of death after cardiovascular disease. The early detection of breast cancer is paramount as it increases the chance of survival.

In the developed and developing world, regular screening for breast cancer is recommended and carried out for women above a certain age, e.g. 40 years old. A screening mammogram is an X-ray image of the breast used to detect changes in breast morphology of women who have no signs or symptoms of breast cancer. It usually involves two X-rays of each breast. Mammograms make it possible to detect tumors that cannot be felt. Mammograms also can find microcalcifications that sometimes indicate the presence of early breast cancer.

A diagnostic mammogram is an X-ray of the breast that is used to check for breast cancer after a lump or other sign or symptom of breast cancer has been found. Signs of breast cancer may include pain, skin thickening, nipple discharge, or a change in breast size or shape. A diagnostic mammogram may take longer than a screening mammogram because it involves more X-rays in order to obtain views of the breast from several angles.

In tomosynthesis, also known as three-dimensional mammography, a quasi 3D image of the breast is created using X-ray exposure of the breast from different angles. When used in addition to usual mammography, it results in more "positive" outcomes of tests, i.e. more findings of possible abnormalities result. However, also the number of false positives can potentially increase. Another concern is that it more than doubles the radiation exposure.

As with all X-rays, mammograms use doses of ionizing radiation to create images. These images are then analyzed for abnormal findings. It is usual to employ lower-energy X-rays, typically Mo (K-shell x-ray energies of 17.5 and 19.6 keV) and Rh (20.2 and 22.7 keV).

False negatives occur when mammograms appear normal even though breast cancer is present. False negatives therefore represent a significant health risk, and it is desirable to improve the quality of medical imaging such that false negatives can be avoided as much as possible.

False positives occur when mammograms are read by a radiologist as abnormal, but no cancer is actually present. When an abnormality is found or suspected, typically a biopsy may be carried out. In the case of a false positive, a biopsy reveals that no cancer is present. Besides the discomfort and trauma caused to a woman in the case of an unnecessary biopsy, the cost of unnecessary biopsies to societies can be significant. It is therefore desirable to reduce false positives in mammograms.

Photon-counting mammography is also known and has been shown to reduce the x-ray dose to the patient compared to conventional methods while maintaining image quality at an equal or higher level.

Photon counting is a technique in which individual photons are counted using a single-photon detector.

A more recent development is to use spectral imaging, which will likely be employed in the new generation of CT scanners, to be able to distinguish between different types of tissue.

In radiology, one of the major disadvantages of X-ray imaging modalities is the negative effect of ionizing radiation. Although the risk from small exposures (as used in most medical imaging) is believed to be relatively small, one way of reducing exposures is to make X-ray detectors as efficient as possible, so that lower doses can be used for the same diagnostic image quality. Photon counting detectors can help, due to their ability to reject noise more easily, and other advantages compared to conventional integrating (summing) charge detectors.

One key feature of photon counting is that it hardly suffers from electronic and detector noise. One can detect photon by photon, which is not possible with conventional radiology imaging systems, in which charges are integrated over a period of time and by the end of the exposure time the charges are digitized. In charge integration mode, the noise is integrated with the signal and later it gets subtracted by measuring the offset signal when there is no X-ray radiation.

Good image resolution in a photon counting imaging device comes generally from two factors: high contrast (i.e. high signal to noise ratio) and spatial resolution. This means that with a decreasing size of an individual detector (or "pixel"), the spatial resolution will improve. For this reason, pixelated detectors are often used.

A pixelated detector herein means that a detector electrode is "segmented", i.e. a single electrode is subdivided into a matrix of pixels. These pixels may generally all have the same size, but this is not necessarily so. The deposit of energy in a detector can thus be registered at the level of individual pixels, rather than at the level of the detector as a whole. The deposit of energy may herein be referred to as an "event". And such a deposit of energy may generally be caused by the decay of a nuclear material. This form of detection is often used in nuclear medical imaging.

Different kinds of detectors are known such as detectors based on scintillating crystals, and so-called semiconductor detectors. Because of the aforementioned spatial resolution, room temperature pixelated solid state detectors based on semiconductor material are generally preferred. When highly energetic photons are "detected" in a semiconductor detector, electron-holes are created. The electrons and holes move in opposite directions towards the electrodes because of a bias voltage applied. In a pixelated detector, the location of registration within the electrodes can be determined due to the fact that the electrodes are pixelated, so that the location of impact within the detector may be determined.

A semiconductor detector in ionizing radiation detection physics is a device that uses a semiconductor (usually silicon or germanium) to measure the effect of incident charged particles or photons. Silicon has a low "Z" and therefore its efficiency to detect X-rays is relatively low. Germanium on the other hand may require cooling down to cryogenic temperatures.

Cadmium telluride (CdTe) and cadmium zinc telluride (CZT) detectors have been developed for use in X-ray spectroscopy and gamma spectroscopy. The high density of these materials means they can effectively attenuate X-rays and gamma-rays with energies of greater than 20 keV that traditional silicon-based sensors are unable to detect. The wide band gap of these materials also means they have high resistivity and are able to operate at, or close to, room temperature (~295K) unlike germanium-based sensors. These detector materials can be used to produce sensors with different electrode structures for imaging and high resolution spectroscopy.

With photon counting one can achieve a high contrast image because the detection system is noise free at the level of electronics and detector leakage current. However, when it comes to the spatial resolution, photon counting can also suffer from small pixel size in a detector.

In the case of an "event", the captured photon in the semiconductor detector generates a small charge cloud with a radius of about 10 μm. Because of the bias voltage, this charge cloud starts to drift to the detector electrode and during this drifting time, the transverse size of the charge cloud expands according the diffusion formula of Fick's law. It can thus happen that the energy of a single event is collected on different pixels. If the energy deposited is above the trigger threshold in more than one pixel, the event thus is counted more than once.

EP 3 262 441 addresses this issue and provides methods and systems for photon counting that avoid double counting of a single event.

The present disclosure provides devices, systems and methods that resolve or at least reduce some of the aforementioned disadvantages.

SUMMARY

In a first aspect, an auxiliary device for a mammography machine is provided. The mammography machine has an X-ray source and an X-ray receptor having a receptor area. The auxiliary device comprises a housing having a length, width, and thickness, wherein the length of the housing is adapted to a length of the receptor area, and the width of the housing is adapted to the width of the receptor area. The auxiliary device further comprises one or more attachments for attaching the auxiliary device to the mammography machine, and a detector inside the housing. The detector of the auxiliary device comprises a slab of semiconductor material, an electrode on a first side of the slab, a second pixelated electrode detector on the second side of the slab, and a read-out circuit bonded to the second pixelated electrode detector. The read-out circuit is configured for spectral photon counting with two or more energy bins.

In accordance with this aspect, an auxiliary device is provided that may be used with a standard mammography machine. The auxiliary device can be positioned in the X-ray receptor area of the mammography machine. The dimensions of the auxiliary device may be adapted for easy placement in the receptor area.

In the small detector area of the auxiliary device, photon counting with different energy bins may be carried out to obtain high quality medical images that may be used to derive the presence of different types of tissues. The detector area is relatively small as compared to the X-ray receptor area of the mammography machine to image a region-of-interest only.

Energy bins are herein to be regarded as ranges or windows of energy levels. When a photon is captured in the semiconductor slab, a charge cloud is formed. For a single event (a single photon capture), the electronic signal measured, usually in voltage, at the pixelated electrode detector is proportional to the amount of energy of the charge cloud.

In some examples, the semiconductor material may be a high Z room temperature semiconductor. A high Z semiconductor is herein to be understood as semiconductor material having a high atomic number. The use of a high Z semiconductor may mean that with a relatively thin slab of material, substantially all of the X-rays may be captured. Suitable examples include: GaAs (Gallium arsenide), CdTe (cadmium telluride), CdZnTe (Cadmium zinc telluride), HgI2 (mercuric iodide), Perovskite, TIBr (Thallium Bromide).

In some examples, the slab of semiconductor material may have a thickness between 0.5 and 3 mm, and specifically between 0.75 and 2 mm. A thin slab of semiconductor material can lead to a thin housing for the auxiliary device. Such a thin device may be more easily used. At the same time, a thickness for the semiconductor material that is sufficient to capture all or at least a large percentage of the X-rays is advantageous.

In some examples, the slab of semiconductor material may have a length that is between 10% and 50% of the length of the receptor area, and may have a width that is between 10% and 50% of the length of the receptor area. In some examples, the slab of semiconductor material may have a length between 5 and 15 cm, and a width between 5 and 15 cm.

In some examples, the read-out circuit may be configured for spectral photon counting with 2-14 energy bins, specifically 3-10 energy bins. It is known that X-ray images using different energy levels, low energy and high energy, can be used to distinguish between different kinds of tissues. With photon counting with the detector explained herein, any number of energy bins may be defined. There is no need to use multiple X-ray doses, instead a single exposure may be sufficient.

The energy bins may have the same "width", but this does not need to be the case. In examples, the energy bins may be programmable. The energy bins may thus be set to levels which are (expected to be) most suitable for a specific implementation. The energy bins may be programmed along the range of the X-ray emission spectrum of the X-ray source of the mammography machine. In an example, the energy bins may be selected such as to maximize the contrast in relation to the k-edge of the contrast agent.

In some examples, the detector of the auxiliary device may further comprise an anti-scatter grid, and optionally wherein the anti-scatter grid is configured to move between a first position covering the detector and a second position not covering the detector. In case of X-rays using Enhanced Contrast Agent, the anti-scatter grid is positioned over the detector. In case of Tomosynthesis mode, the anti-scatter grid may be removed from the detector.

In some examples, the attachment means for attaching the auxiliary device to the imaging machine may comprise one or more of the following: clips, belts, releasable adhesive, suction cups, and vacuum regulated fasteners.

In some examples, the housing may have a length between 20 and 30 cm, and a width between 15 and 25 cm. The housing may be adapted to fit precisely on the receptor area of the mammography machine, such that a professional may easily correctly position the auxiliary device. The area of the detector may be visibly or marked on the housing, such that the region of interest may be correctly positioned with respect to the detector.

In a further aspect, a method for providing a medical image of a region of interest is provided. The method comprises providing the auxiliary device according to any of the examples described herein. The auxiliary device is attached to a receptor area of a mammography machine, and then a breast of a subject may be positioned such that the region of interest is positioned between the detector of the auxiliary device and the X-ray source. The method then comprises activating the mammography machine to send X-rays and absorbing the X-rays in the detector, and generating the medical image of the region-of-interest based on the X-rays absorbed in the detector.

In some examples, the region-of-interest may be determined prior to providing the medical image of the region of interest, and the region-of-interest may be selected from a mammogram. A mammography machine may be used to provide a diagnostic or screening mammogram. If there is a suspicion of a tumor in an area, in many cases a biopsy would be scheduled normally. With the devices and methods of the present disclosure, before planning a biopsy, a region of interest, i.e. a region in which there might be a tumor, can be imaged.

In some examples, generating the medical image may comprise generating a first medical image a first energy bin, and generating a second medical image for a second energy bin. Two, three or more energy bins may be defined, and for each of the energy bins, a medical image may be generated. The different energy levels can give information on different types of tissue.

In some examples, the subject has previously been administered an enhanced contrast agent.

In some examples, the method may further comprise analyzing the medical image of the region-of-interest, particularly using a computer algorithm, and more particularly wherein the computer algorithm has been generated with artificial intelligence. The present disclosure provides possibilities of deriving different types of tissue which are currently not used for diagnostic purposes. At present, maximum two different energy levels have been used to distinguish between types of tissue. By using a mathematical model derived from machine learning, new and improved analyses of the medical images may be obtained.

BRIEF DESCRIPTION OF THE DRAWINGS

Non-limiting examples of the present disclosure will be described in the following, with reference to the appended figures, in which.

The figures refer to example implementations and are only used as an aid for understanding the claimed subject matter, not for limiting it in any sense.

DETAILED DESCRIPTION

Figure 1A:
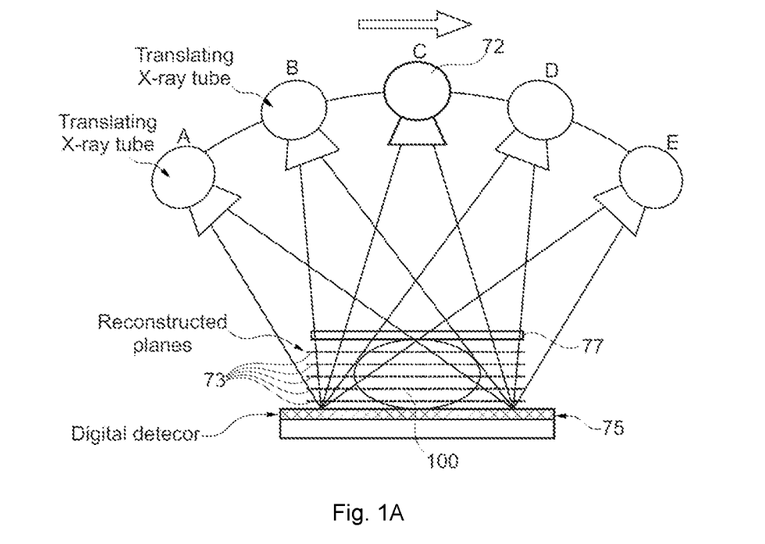
FIGS. 1A and 1B illustrate the principle of tomosynthesis and of a tomosynthesis machine.
Figure 1B:
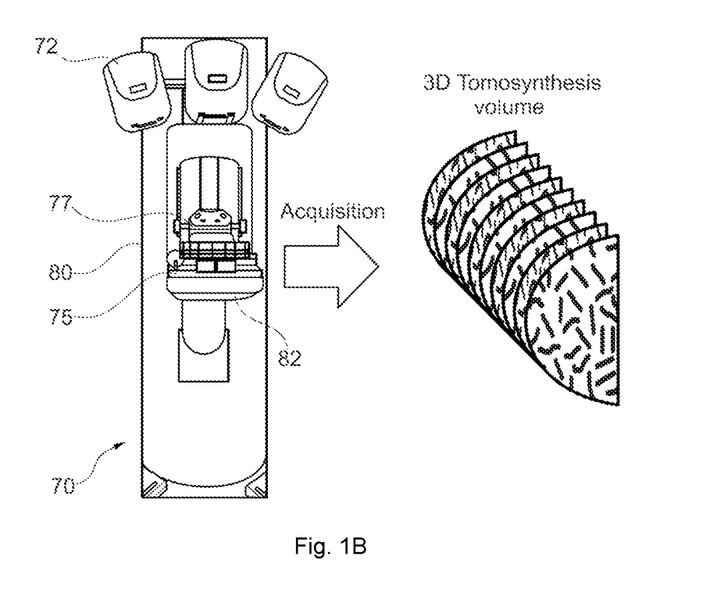

FIGS. 1A and 1B schematically illustrate the principle of tomosynthesis and of a tomosynthesis machine 70. In tomosynthesis, a quasi 3D image of the breast is created using X-ray exposure of the breast from different angles.

A mammography machine for tomosynthesis may comprise a fixture or frame 80 supporting a receptor area 75 on platform 82 and an X-ray tube 72. A subject's breast 100 may be placed on top of the receptor area 75 and may be compressed between the receptor area 75 and a compression plate 77.

The X-ray tube 72 may be moved in different positions A, B, C, D, and E and the breast may be exposed to ionizing radiation from each different position of the X-ray tube 72. Because the breast 100 is imaged from different angles, the images from these different angles can be combined to reconstruct images at different imaging planes 73.

Figure 2A:
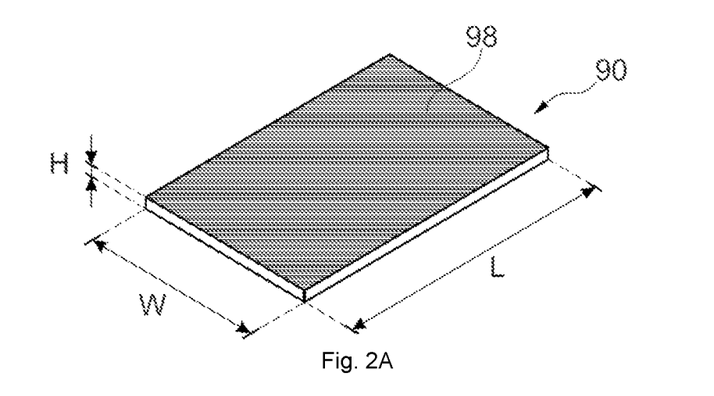
FIGS. 2A-2C schematically illustrate an auxiliary device according to an example.
Figure 2B:
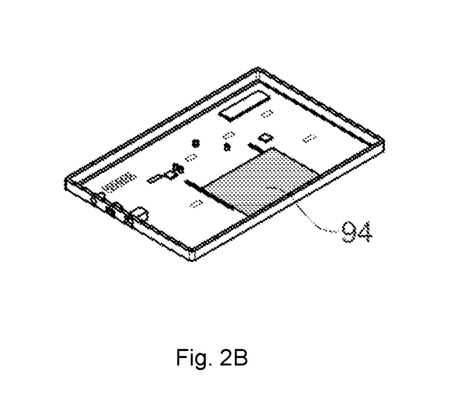
Figure 2C:
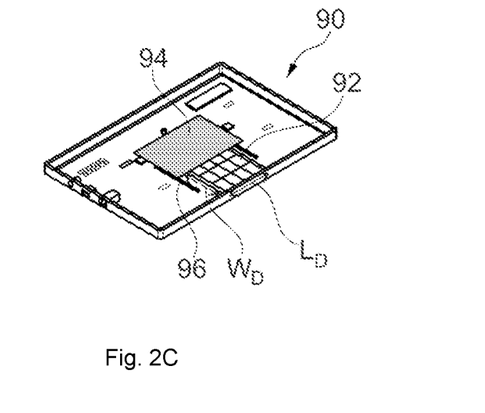

FIGS. 2A-2C schematically illustrates an auxiliary device according to an example of the present disclosure.

FIG. 2A illustrates an auxiliary device 90 for a mammography machine 70, the mammography machine 70 having an X-ray source 72 and an X-ray receptor 75 having a receptor area. The auxiliary device 90 comprises a housing 98 having a length L, width W, and thickness H, wherein the length L of the housing 98 is adapted to a length of the receptor area $L_R$, and the width of the housing is adapted to the width of the receptor area $W_R$. The length and width $L_R$ and $W_R$ of the receptor area may be seen more clearly e.g. in FIG. 3A.

The length L and width W of the housing 98 of the auxiliary device may be adapted to the length and width of the receptor area, such that the length L and width W substantially correspond to the length and width $L_R$ and $W_R$ of the receptor area. The length and width of the housing 98 may also be slightly smaller than the corresponding length and width of the receptor area of the mammography machine. In general, the length and width of the housing 98 may be such as to facilitate positioning of the auxiliary device 90 on the receptor area.

In some examples, the housing may have a length between 20 and 30 cm, and a width between 15 and 25 cm. Suitable dimensions of the housing depend particularly on the mammography machine with which it is to be used. Different mammography machines from different suppliers have different dimensions for the detector area. In general, a detector for a mammography machine may have a width of between 15 and 25 cm, and specifically between 18 and 24 cm, and have a length between 20 and 30 cm, specifically between 23 and 30 cm. The dimensions of the auxiliary device 90 may be determined to be such that the auxiliary device fits exactly on the receptor area, without protruding beyond the detector on any side. In other examples, the auxiliary device may be slightly smaller than the receptor area. In general, the dimensions of the auxiliary device should not be much greater than the dimensions of the receptor area of the mammography machine, since this can complicate correct positioning of the auxiliary device.

The auxiliary device 90 further comprises one or more attachments (non-illustrated) for attaching the auxiliary device to the mammography machine. The attachment points, fasteners or further attachment means may fix the auxiliary device 90 securely in place in operation.

The auxiliary device further includes a detector 92 inside the housing 98. The detector 92 comprises a slab of semiconductor material, an electrode on a first side of the slab, and a second pixelated electrode detector on the second side of the slab, and a read-out circuit bonded to the second pixelated electrode detector. The position of the detector 92 inside the housing may be indicated or visible on the outside of the housing. An operator may thus position the auxiliary device 90 knowing precisely where the detector 92 is located.

Figure 5A:
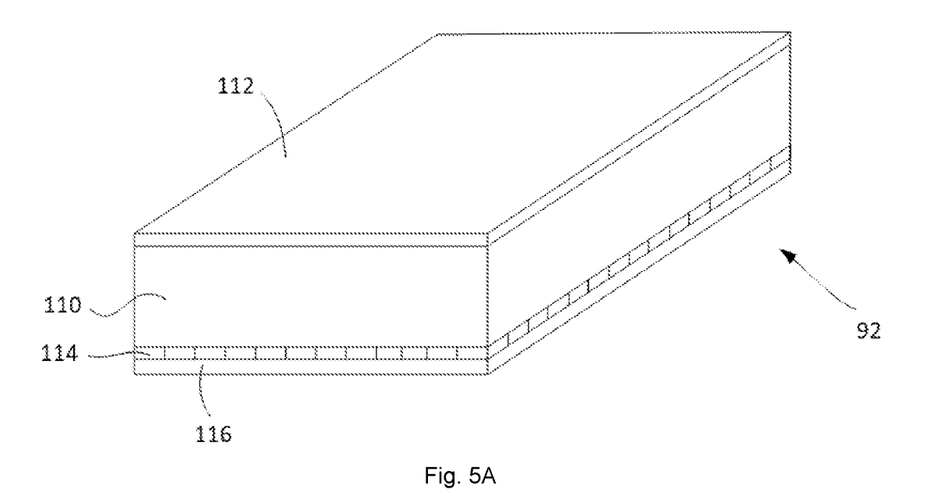
FIGS. 5A and 5B schematically illustrate an example of a pixelated semiconductor detector.

One example of a suitable detector build-up is illustrated in WO 2010/034619 and in WO 2018/019941. Reference may be had to FIG. 5A: a detector 92 in particular may include a slab 110 of e.g. a high Z room temperature semiconductor, specifically one of the following semiconductors may be used: GaAs, CdTe, CdZnTe, HgI2, Perovskite, TlBr.

The slab 110 of the semiconductor material may have a thickness e.g. between 0.2 and 3 mm, and specifically between 0.75 and 2 mm. As will be explained herein, due to the use of the auxiliary device, it is beneficial to make the detector 92 and the housing 98 relatively thin such that a breast may be positioned on top of the auxiliary device positioned on the mammography machine in substantially the same manner as if the auxiliary device were not present.

On one side of the slab, a first electrode 112 may be provided, e.g. a cathode 112. On the other side of the slab, a pixelated electrode detector 114 may be provided. The pixelated electrode 114 may be the anode.

The electrodes 112, 114 may provide a bias voltage. In the case of an "event", the captured photon in the semiconductor detector generates a small charge cloud with a radius of about 10 μm. Because of the bias voltage, this charge cloud starts to drift to the detector electrode.

The pixelated detector 114 may be mounted on top of a read-out circuit 116. The read-out circuit 116 may be an ASIC (Application Specific Integrated Circuit). The read-out circuit 116 may be bonded directly to the pixels. In particular, bump bonding may be used.

The pixelated detector 114 comprises a plurality of pixels. An event may be registered in a single pixel. Or potentially it could be registered in multiple pixels. In order to properly apply photon counting with a small pixel size, and avoid double counting, a configuration such as illustrated in WO 2016/135106 may be used.

Figure 3A:
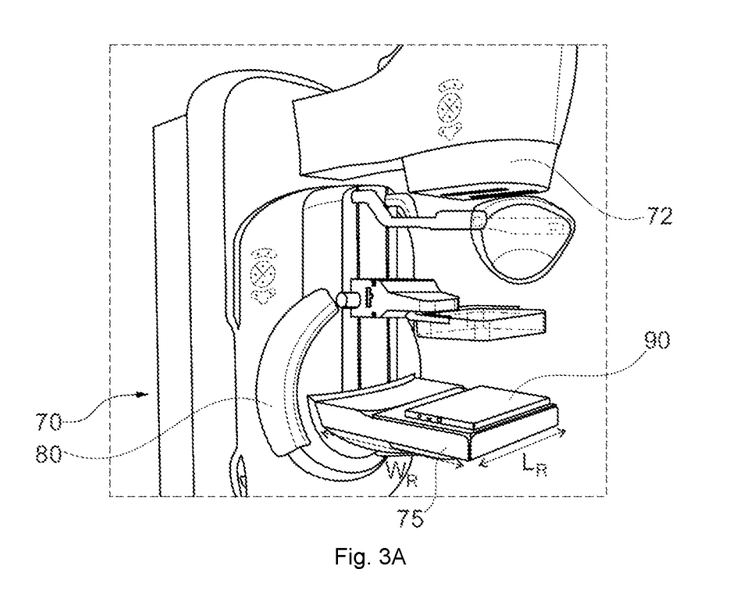
FIGS. 3A and 3B schematically illustrate an example of how to use an auxiliary device for a mammography machine.
Figure 3B:
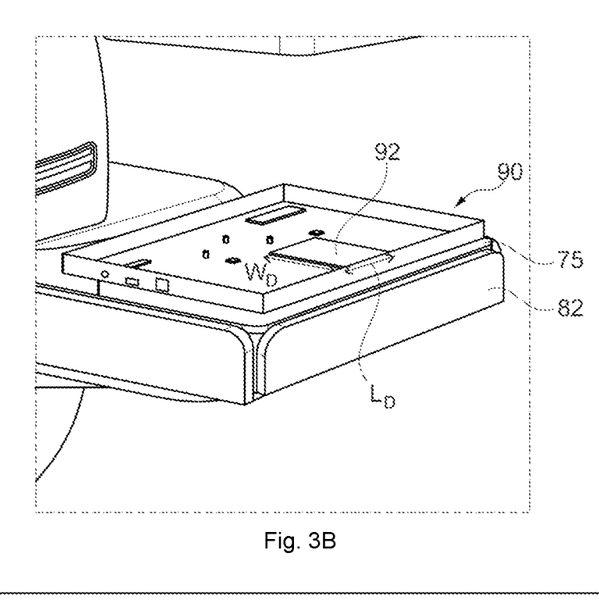
Figure 4:
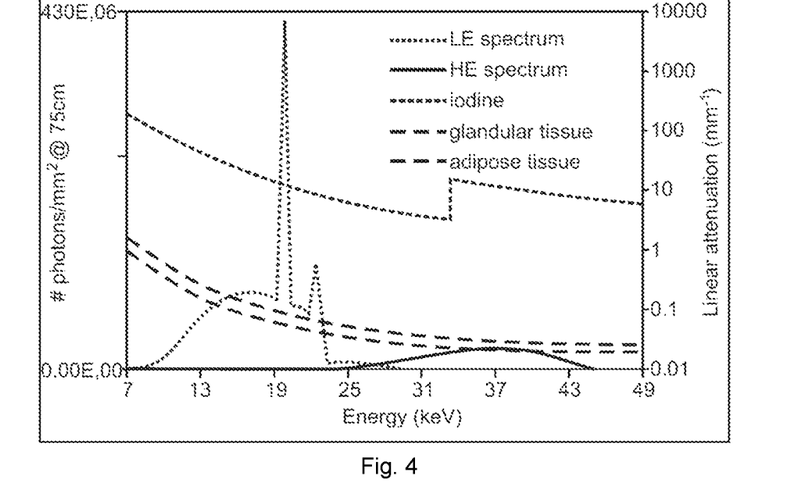
FIG. 4 illustrates attenuation factors for different types of tissues and the composition of different X-ray shots.
Figure 5B:
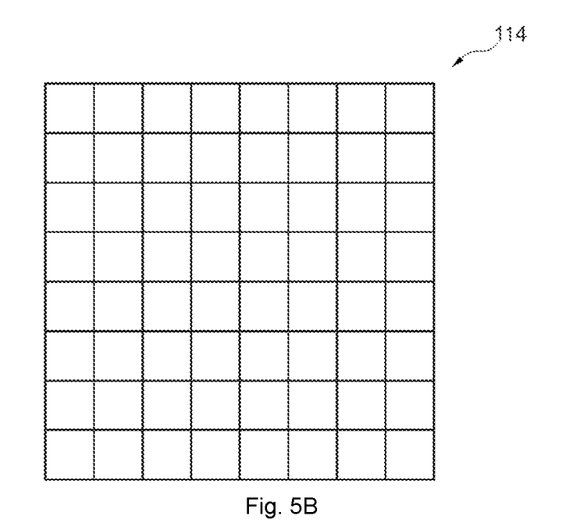

One way of avoiding double counting has been described in WO 2016/135106, and particularly in FIGS. 3-5 and corresponding parts of the description. The technique described is based on registering the charge in a single pixel only, and the charge is assigned to the pixel receiving the highest part or proportion of the charge.

In particular, the registration of a charge in a pixel may occur with a delay. The delay is decreased as the charge received increases. This means that the pixel receiving the highest charge (and this may be registered as the highest peak voltage of a pulse as generated in a shaper connected to the individual pixel) registers a charge first. All neighboring pixels (and these may be pixels directly neighboring the pixel in question, or other pixels with which charge sharing may occur) may then be inhibited or otherwise avoided from counting the same event.

The read-out circuit may be programmed such that when a pixel registers a charge, this is communicated to the neighboring pixels. These neighboring pixels then do not count the charge belonging to the same event. The neighboring pixels however can determine the charge received in those pixels. As a result, a total charge for an event may be determined and assigned to a single pixel, namely the pixel receiving the highest part of the charge.

WO 2016/135106 gives a number of ways of achieving this. Particularly, different trigger levels may be defined with different delays. Also, registration may be accomplished upon discharge of a capacitor to a reference level, and the reference level is a function of the charge received. The disclosure of WO 2016/135106 is herein incorporated entirely by reference.

The read-out circuit of the auxiliary device 90 may be configured for spectral photon counting with two or more energy bins. Energy bins are herein to be regarded as ranges or windows of energy levels. When a photon is captured in the semiconductor slab, a charge cloud is formed. For a single event (a single photon capture), the electronic signal measured, usually in voltage, at the pixelated electrode detector is proportional to the amount of energy of the charge cloud. By defining different energy ranges, events of different nature may be separated from each other.

By photon counting correctly, i.e. identifying individual events correctly, and avoiding double or triple counting of the same event, the total energy deposit of every single event can be determined. Different tissues have different absorption characteristics for photons of different energy levels. By distinguishing different events of different energy levels, the location of different types of tissue may be more accurately derived.

As may be seen in FIGS. 2B and 2C, dimensions of the detector 92 may be significantly smaller than the dimensions of the housing 98 and of the receptor area of the mammography machine. In some examples, the slab of semiconductor material may have a length Lo that is between 10% and 50% of the length of the receptor area, and may have a width Wo that is between 10% and 50% of the length of the receptor area. In some examples, the slab of semiconductor material has a length Lo between 5 and 15 cm, and a width $W_D$ between 5 and 15 cm. It should be clear that the slab of semiconductor material may be built up from various smaller slabs. E.g. a slab of 15×15 cm may be built up from multiple slabs of 5×5 cm.

The reduced dimensions of the detector 92 are sufficient for imaging of a region-of-interest (ROI) and reduce its production cost significantly. In examples, a mammogram may be generated using a mammography machine 70. Within the mammogram, a region-of-interest may be defined wherein suspicious tissue may be located. Before performing a biopsy to determine whether the suspicious tissue is benign or malignant, the auxiliary device 90 may be positioned on the same mammography machine 70.

The ROI may be imaged using spectral photon counting of the auxiliary device. There is no need for the whole receptor area to be configured for spectral photon counting. It may be sufficient to provide the high resolution imaging only for the region of interest.

In the example of FIGS. 2A-2C, the auxiliary device may furthermore comprise an anti-scatter grid 94. In some examples, the anti-scatter grid may be configured to move between a first position covering the detector (see FIG. 2B) and a second position not covering the detector (FIG. 2C). In further examples, an anti-scatter grid with an adaptable of attenuation may be used.

An anti-scatter grid is a device for limiting the amount of radiation scatter created in a radiographic exposure reaching the detector. Such a grid may be constructed of a series of alternating parallel strips of lead and a radiolucent substance such as a plastic, carbon fiber, aluminum, even paper. The grid may be placed between the patient and the detector during the exposure. Primary beam radiation passes through the radiolucent strips as it travels roughly parallel to them, but scattered radiation which may have deviated from the parallel beam, cannot easily pass through the grid as it encounters the lead strips at an angle, and is attenuated, or lost, from the beam.

Grids may be used particularly in examinations where a large quantity of scatter is created, i.e., those involving a large volume of tissue being irradiated and those requiring low energy i.e. voltage. The scatter would otherwise degrade the image by reducing the contrast and resolution. Use of a grid, however, requires a greater radiation exposure to the patient as a substantial part of the primary beam can also be attenuated by the lead slats, and for this reason grids are not used for all examinations.

The anti-scatter grid 94 may be slidable between one position and another along guides 96. The anti-scatter grid may be moved e.g. by an electric motor, or any other actuator or may be manually moved. When the auxiliary device is used for imaging with X-rays and Enhanced Contrast Agent, the anti-scatter grid may be positioned over the detector. When the auxiliary device is used in tomosynthesis mode for example, the anti-scatter grid may be in a second position not covering the detector. The auxiliary device can thus be adapted for different modes or different mammography machines.

FIGS. 3A and 3B schematically illustrate an example of how to use an auxiliary device 90 for a mammography machine 70. FIG. 3 illustrates how the auxiliary device may be attached to the receptor area 75. The auxiliary device 90 may comprise attachments for attaching the auxiliary device 90 to the mammography machine. The attachments may include e.g. clips, or belts to mechanically fix the auxiliary device 90 to the mammography machine 70. E.g. the clips may clip around the platform 82.

Alternatively or additionally, the auxiliary device 90 may be attached using a releasable adhesive, or suction cups, or vacuum regulated fasteners. In a specific example, a backside of the auxiliary device 90 may have a vacuum release silicon layer to insure firm contact on the top of the mammography detector. When no vacuum is applied (default state) the auxiliary device latches firmly to the surface of the mammography detector as depicted. By applying vacuum to the silicon pad, the auxiliary device can be moved, e.g. removed or repositioned. A small vacuum pump may be used to attach or detach the auxiliary device.

Vacuum regulated fasteners of this type are commercially available from Gel-Pak®.

The auxiliary device 90 may be designed to operate standalone, i.e. independent from any mammography machine. The auxiliary device 90 may thus be operable with mammography machines of different types and brands.

A "pre-shot" may be used with the same filter, kV, mA as for a "standard" mammogram, but with 1% of the original time. From this information, an operator may determine and consequently set the final time shutter for the X-ray tube to get enough X-ray flux for an image with the photon counting detector with good Signal-to-Noise ratio.

FIG. 4 illustrates attenuation factors for different types of tissues and the composition of different X-ray shots. In some examples, the read-out circuit may be configured for spectral photon counting with 2-14 energy bins, specifically 3-10 energy bins.

In an example, the detector may have 8 energy levels and this implies that in one single X-ray exposure one can obtain 8 images of the same object and each of these images is related to specific X-ray photons that belong to a certain window of energy. This feature allows capturing the 8 images of the breast tissue, after injecting Iodine as enhanced contrast agent (ECA), with a single X-ray exposure, plus precise definition for energy windows, and without the attenuation of the high energy X-ray flux. In the prior art, to provide an ECA image with high energy X-ray photons, the low energy X-ray flux is eliminated but this can eliminate a part of the high Energy flux as well.

Each energy window (or "energy bin") corresponds to a different attenuation factor. The attenuation factor indicates a possible material with certain composite density. For example, it has been documented that malignant tissue in the breast tends to have high elevation of Na in the microcalcifications. Also, it has been reported that for a low average ratio of Na to Ca (3.3%) in a micro-calcification lesion, the tumor is typically benign. However when this ratio is high (e.g. 5% or more) the tumor may be malignant.

Such a change of ratio may be picked up with a multi-energy bin photon counting detector, in particular when coupled with artificial intelligence.

The different energy levels can be chosen in accordance with circumstances and preferences. In the example with 8 energy bins, one energy level may be placed at the k-edge of Iodine (33.2 KeV) and the others may be distributed along the full spectrum of the X-ray tube.

Figure 6:
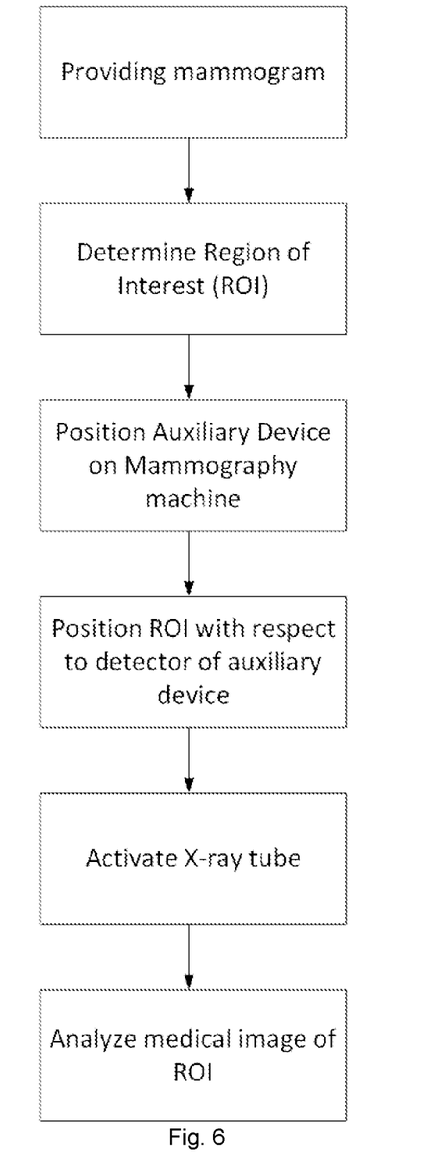
FIG. 6 illustrates a flowchart of an example of a method for using an auxiliary device according to the present disclosure.

FIG. 6 schematically illustrates a flowchart of a method for providing a medical image of a region of interest. The method in this example comprises providing a (standard) mammogram. The mammogram may be produced with a mammography machine. A Region of Interest (ROI) may be selected from the mammogram. For example, a medical professional may select an area of the mammogram with suspicious tissue.

Then, the auxiliary device according to any of the examples disclosed herein may be provided. The auxiliary device may be attached to a receptor area of a mammography machine. Then, a breast of a subject may be placed such that the region of interest is positioned above the detector of the auxiliary device. In some examples, the subject may have previously been administered an enhanced contrast agent.

Then, the mammography machine may be activated (i.e. the X-ray tube may be activated) to send X-rays and then to absorb the X-rays in the detector. The same mammography machine as was used for the first mammogram may be used. A medical image of the region-of-interest based on the X-rays absorbed in the detector of the auxiliary device may be generated.

The setting of the mammography machine may be used but with 0.01% of the dose. Since the detector of the auxiliary device is a photon counting detector, it is immune to sporadic noise and therefore the shutter can be open before the activation of X-ray tube of the mammography machine.

When the X-ray tube is activated, the photon counting detector may sense high correlated triggers in many pixels during a window of time that can be configured, e.g. 10 microseconds. This will be considered as the flag that the X-ray exposure has started.

The end of the shutter may be configured such that it closes after the same window of time (e.g. 10 microseconds) of not detecting a flux of X-ray photons and this may be considered as the X-ray tube is in OFF state.

With such a setting, the auxiliary device may be used in combination with different mammography machines, even if the manufacturer of the mammography machine has not shared any of the settings of the machines and if the user interface of the mammography machine does not allow any of the settings to be changed.

In some examples, generating the medical image may comprise generating a first medical image for a first energy bin, and generating a second medical image for a second energy bin.

The image format may be in DICOM format and may be sent from the detector to a viewer via Ethernet or via WiFi.

In examples, further images for further energy bins may be provided. The different images may be used to determine different types of tissue. The combination of the different images for different energy bins may be used together to derive a composition of tissue of the ROI.

In some examples, analyzing the medical image of the region-of-interest may be carried out using a computer algorithm. Particularly, the computer algorithm may have been generated with artificial intelligence. One example of artificial intelligence that may be used is an artificial or deep neural network. Artificial neural networks may be particularly useful in image processing.

Neural networks can learn by processing examples, each of which contains a known "input" and "result," forming probability-weighted associations between the two, which are stored within the data structure of the artificial neural network itself.

After being given a sufficient number of examples (i.e. after sufficient training), the network becomes capable of predicting results from inputs, using the associations built from the example set. If a feedback loop is provided to the neural net about the accuracy of its predictions, it continues to refine its associations, resulting in an ever-increasing level of accuracy.

A training set may be composed of existing mammograms, and particularly mammograms for different X-ray levels. These mammograms may be linked with results of breast biopsies. The training may set be expanded by medical images provided by the auxiliary device. As more medical images are collected, the artificial neural network may improve.

Other types of machine learning such as Support Vector Machines, linear regression logistic regression, and k-nearest neighbor algorithms may be used as well.

Even though the present disclosure has focused on the use of auxiliary devices with a mammography machine, wherein the auxiliary device may be positioned on top of the receptor area of the mammography machine, and a breast may be positioned on top of the auxiliary device. In other examples however, other imaging machines may be used, and a body part of a subject may be positioned between the detector area of the auxiliary device and an X-ray source of the imaging machine. A specific example is a prone biopsy machine.

Although only a number of examples have been disclosed herein, other alternatives, modifications, uses and/or equivalents thereof are possible. Furthermore, all possible combinations of the described examples are also covered. Thus, the scope of the present disclosure should not be limited by the particular examples disclosed herein.

What is claimed is:

1. An auxiliary device for a mammography machine having an X-ray source and an X-ray receptor having a receptor area, the auxiliary device comprising:
   a housing that is attachable to the mammography machine and sized to fit over the receptor area of the mammography machine;
   one or more fasteners that are configured to attach the housing to the mammography machine in a releasable manner;
   a detector located inside the housing that is configured to be located on the receptor area upon the housing being attached to the mammography machine, the detector including:
      a slab of semiconductor material, the slab of semiconductor material having a length that is between 10% and 50% of a length of the receptor area of the mammography machine;
      an electrode on a first side of the slab, the electrode configured to face the receptor area;
      a pixelated electrode detector on a second side of the slab opposite the first side of the slab;
      a read-out circuit bonded to the pixelated electrode detector, the read-out circuit being configured for spectral photon counting with two or more energy bins.

2. The auxiliary device of claim 1, wherein the semiconductor material is a high Z room temperature semiconductor.

3. The auxiliary device of claim 1, wherein the semiconductor material is selected from the group consisting of GaAs, CdTe, CdZnTe, HgI2, Perovskite and TlBr.

4. The auxiliary device of claim 1, wherein the slab of semiconductor material has a thickness between 0.2 and 3.0 mm.

5. The auxiliary device of claim 1, wherein the slab of semiconductor material has a width that is between 10% and 50% of a width of the receptor area of the mammography machine.

6. The auxiliary device of claim 1, wherein the slab of semiconductor material has a length between 5 and 15 cm, and a width between 5 and 15 cm.

7. The auxiliary device of claim 1, wherein the read-out circuit is configured for spectral photon counting with 2-14 energy bins.

8. The auxiliary device of claim 1, wherein the read-out circuit comprises an ASIC.

9. The auxiliary device of claim 1, further comprising an anti-scatter grid.

10. The auxiliary device of claim 9, wherein the anti-scatter grid is configured to move between a first position covering the detector and a second position not covering the detector.

11. The auxiliary device of claim 1, wherein an area of the detector is visible through the housing or marked on the housing such that a region of interest of a breast of a subject may be correctly positioned with respect to the detector.

12. The auxiliary device of claim 1, wherein the housing has a length between 20 and 30 cm, and a width between 15 and 25 cm.

13. A method for providing a medical image of a region of interest in a breast of a subject, the method comprising:
   providing the auxiliary device of claim 1;
   attaching the auxiliary device to a receptor area of a mammography machine;
   placing the breast of the subject such that the region of interest is positioned between the detector of the auxiliary device and an X-ray source of the mammography machine;
   activating the mammography machine to send X-rays and absorbing the X-rays in the detector; and
   generating the medical image of the region-of-interest based on the X-rays absorbed in the detector.

14. The method of claim 13, further comprising determining the region-of-interest prior to providing the medial image of the region of interest, and wherein the region-of-interest is selected from a mammogram.

15. The method of claim 14, wherein the mammogram is generated with the mammography machine.

16. The method of claim 13, wherein generating the medical image comprises generating a first medical image for a first energy bin, and generating a second medical image for a second energy bin.

17. The method of any of claim 13, wherein the subject has previously been administered an enhanced contrast agent.

18. The method of claim 13, further comprising analyzing the medical image of the region-of-interest using a computer algorithm.

19. The method of claim 18, wherein the computer algorithm has been generated with artificial intelligence.

* * * * *

UNITED STATES PATENT AND TRADEMARK OFFICE
CERTIFICATE OF CORRECTION

PATENT NO. : 11,766,228 B2
APPLICATION NO. : 17/467621
DATED : September 26, 2023
INVENTOR(S) : Mokhtar Chmeissani Raad It is certified that error appears in the above-identified patent and that said Letters Patent is hereby corrected as shown below:

In the Specification

Column 8, Line 32, change "Lo" to -- $L_D$ --;

Column 8, Line 34, change "Wo" to -- $W_D$ --; and

Column 8, Line 36, change "Lo" to -- $L_D$ --.

Signed and Sealed this
Twentieth Day of February, 2024

*Katherine Kelly Vidal*
Katherine Kelly Vidal
*Director of the United States Patent and Trademark Office*